United States Patent [19]

O'Halloran et al.

[11] Patent Number: 5,786,496
[45] Date of Patent: Jul. 28, 1998

[54] HIGH OXIDATION STATE METAL OXO COMPLEXES OF THE PHAB LIGAND

[75] Inventors: Thomas V. O'Halloran, Kenilworth, Ill.; Frederick M. MacDonnell, Norwood, Mass.; Nathanael L. P. Fackler, Chicago, Ill.

[73] Assignee: Northwestern University, Evanston, Ill.

[21] Appl. No.: 746,617

[22] Filed: Nov. 15, 1996

Related U.S. Application Data

[63] Continuation of Ser. No. 294,145, Aug. 22, 1994, abandoned.

[51] Int. Cl.$^6$ .................. C07F 15/00; C07C 233/00; C07C 45/00; A61K 51/00
[52] U.S. Cl. .................. 556/137; 564/158; 568/14; 568/17; 568/426; 549/523; 549/337; 424/1.65; 424/9.36; 534/10; 534/15
[58] Field of Search .................. 564/158; 556/137, 556/42, 45, 32, 34, 56, 57; 568/27, 485, 489, 14, 17, 426; 549/337, 510, 523, 524, 537; 424/1.65; 534/10, 14, 15, 16

[56] References Cited

U.S. PATENT DOCUMENTS 4,577,042 3/1986 Collins et al. .
4,758,682 7/1988 Collins et al. .

FOREIGN PATENT DOCUMENTS

WO 91/14694 10/1991 WIPO .
WO 93/03838 3/1993 WIPO .

OTHER PUBLICATIONS

Caplus, Caplus Search Report, AN; 1985:487739 Caplus, Bolotov et al., Khar'k Farm. Zh., 18(5), 552–4, (1984).
Anson et al., Highly Stabilized Copper (III) Complexes, J. Am. Chem. Soc., 109, 2974–2979, (1987).
Lee et al., "Photochemistry of a Square–Planar Cobalt (III) Complex", Inorg. Chem., 29, 2015–2017, (1990).
Bolotov et al., "Synthesis, Properties and Biological Activity of 3,3,3'–3',3'–Tetraphenyl–5, 5'–bis(2–Oxoindoline–1–Acetic Acids)", Khim.–Farm. Zh. (1984), 18(5), 552–4, Chem. Abs No. 103:87739.
Andersson and Sharpless, "A Dramatic Ligand Effect on the Relative Reactivities of Substituted Alkenes with Osmium Tetroxide," J. Am. Chem. Soc., 115:7047–7048 (1993).
Anson, et al., "Highly Stabilized Copper(III) Complexes," J. Am. Chem. Soc., 109:2974–2979 (1987).

MacDonnell, et al., "Air Oxidation of a Five–Coordinate Mn(III) Dimer to a High–Valent Oxomanganese(V) Complex," J. Am. Chem. Soc., 116:7431–7432 (1994).
Collins and Gordon-Wylie. "A Manganese(V)–Oxo Complex," J. Am. Chem. Soc., 111:4511–4513 (1989).
Collins, et al., "A Water–Stable Manganese(V)–Oxo Complex: Definitive Assignment of a $v_{Mn\equiv O}$ Infrared Vibration," J. Am. Chem. Soc., 112:899–901 (1990).
Jacobsen, et al., "Electronic Tuning of Asymmetric Catalysts," J.Am. Chem. Soc., 113:6703–6704 (1991).
Reagent of the Year 1994, Fluka Prize 1994, Fluka Chemie AG, Buchs, Switzerland, 1994.
Gobel and Sharpless, "Temperature Effects in Asymmetric Dihydroxylation: Evidence for a Stepwise Mechanism," Angew. Chem. Int. Ed. Engl., 32(9):1329–1331 (1993).
Lee, et al., "Enantiomerically Pure Expoychromans via Symmetric Catalysis," Tetra. Lett., 32(28):5055–5058 (1991).
MacDonnell, et al., "Oxidation of Organic Substrates Utilizing a Manganese(III)–Oxomanganese(V) Catalyst and Dioxygen," abstract, 206th American Chemical Society Meeting, Aug. 22–27, 1993, Chicago, IL.
Mazzi, et al., "How a technetium complex becomes a radiopharmaceutical," Lectures in Bioinorganic Chemistry, Nicolini et al . . . , eds., Cortina International, Verona, Italy, 1991, pp. 91–101.
O'Halloran, et al., "Structure and Reactivity of Five Coordinate Terminal Oxo Complexes of Chromium, Manganese and Ruthenium," abstract, 207th American Chemical Society National Meeting, Mar. 13–17, 1994, San Diego, CA.
Workman, et al., "Vibrational and Electrochemical Properties of a Series of Stable Manganese(V)–Oxo Complexes," Inorg. Chem., 31:1548–1550 (1992).
Mazzi et al., "Technitium coordination chemistry: development of new backbones for $^{99m}$Tc raadiopharmaceuticals," Technetium and Rhenium in Chemistry and Nuclear Medicine 3, Nicolini et al., Eds., Raven Press, New York, pp. 39–50, 1983.

Primary Examiner—Gary E. Hollinden
Assistant Examiner—Michael G. Hartley
Attorney, Agent, or Firm—Edward J. Timmer

[57] ABSTRACT

The present invention provides a new tetradentate bis-amido bis-alkoxo, 1,2-(bis-2,20diphenyl-2-hydroxyethanamido) benzene (H$_4$PHAB) and various derivatives thereof. This ligand is able to stabilize high valen metal oxo complexes by providing strong sigma donor ligands and through the use of steric bulk to prevent decomposition via formation of the μ-oxo dimers. Disclosed are novel metal oxo structural chemistry and oxidation reactions carried out with the novel metal oxo complexes.

8 Claims, 7 Drawing Sheets

FIG. IA

H₄PHAB, R=Hydrogen
H₄Me₂PHAB, R=Methyl

H₄BP-PHAB

DAMA

CATALYSIS

Hydroxylation $$\xrightarrow[{[MnPHAB]_2^{2-}}]{O_2}$$

Oxotransfer $Ph_3P \xrightarrow[{[Ru(O)PHAB]^{1-}}]{O_2} Ph_3P=O$

Epoxidation $$\xrightarrow[\substack{[MnPHAB]_2^{2-} \\ \text{or} \\ [Fe(Cl)PHAB]^{2-}}]{PhIO}$$

HIGH OXIDATION STATE METAL OXO COMPLEXES OF THE PHAB LIGAND

This application is a continuation of U.S. Ser. No. 08/294 145, filed Aug. 22, 1994, now abandoned.

The U.S. Government owns rights in the present invention pursuant to the National Science Foundation Presidential Young Investigator Award CHE8657704.

BACKGROUND OF THE INVENTION

1. Field of the Invention

The present invention relates generally to the field of metal oxo complexes. More particularly, it concerns the development of novel ligand systems for the stabilization of metals in high oxidation states and the role of these complexes in the catalytic oxidation of organic substrates with molecular oxygen and oxidants such as ROOH and iodosylbenzene.

2. Description of the Related Art

The role of oxo metal complexes in the catalytic oxidation of organic substrates with molecular oxygen is of central importance in aerobic life and industrial oxidations (Ingraham & Meyer, 1985). Considerable attention has focused on mimicking the reactions of the heme iron center in cytochrome P450 (Spiro et al., 1980) and non-hemecenters of methane monooxygenase (MMO) (Sheldon & Kochi, 1981) due to their ability to selectively oxidize organic substrates with dioxygen under ambient conditions. The best model systems developed thus far are the metalloporphyrin complexes. However, simple metalloporphyrin systems are unable to directly use dioxygen, but instead require reduced forms of dioxygen, such as $H_2O_2$, ROOH, iodosylbenzene (PhIO) or NaOCl. A few systems have been developed to address this issue using a variety of first row transition-metal complexes to activate dioxygen or facilitate oxygen atom transfer to organic substrates (Ellis & Lyons, 1991; Sheldon & Kochi, 1981; Jones et al., 1979; Holm, 1987; Jacobsen et al., 1991; Mukaiyama et al., 1993; Srinivasan & Kochi, 1985; Siddall et al., 1983; Collman et al., 1975). In many cases the reactive species is assumed to be the terminal oxo group of a high-valent metal complex, but few such complexes have been isolated and structurally characterized (Srinivasan & Kochi, 1985; Siddall et al., 1983; Collins & Gordon-Wylie, 1989; Anson et al., 1987; Collins et al., 1990; Workman et al., 1992).

A major difficulty in the isolation of these complexes, particularly ferryl and manganyl porphyrin compounds, is the ease with which they decompose into the μ-oxo dimers. The incorporation of steric bulk to prevent this μ-oxo dimerization has been demonstrated by the picket-fence porphyrins (Collman et al., 1975). However, this alone could not stabilize ferryl or manganyl complexes for a thorough structural investigation. Furthermore, these complexes have not been demonstrated to have useful catalytic activity.

Progress has also been made in the development of oxidation-resistant tetradentate ligands (Collins & Gordon-Wylie, 1989; Anson et al., 1987; Collins et al., 1990; Workman et al., 1992) which have also been synthesized. It has been shown that bis-amido, bis-alkoxo donor sets can stabilize high oxidation state metal oxo complexes (Collins & Gordon-Wylie, 1989; Anson et al., 1987; Collins et al., 1990; Workman et al., 1992). However, while the stability of these complexes has been demonstrated their catalytic activity has not.

Dioxygen reactions with Mn(II) complexes are well precedented, but $O_2$ reactions with metal ions in the +3 oxidation state are rare and, in the case of most Mn(III) complexes, result in Mn(IV)-oxo-or-peroxo-bridged dimers or the Mn(IV) one-electron oxidation product (Ghodes & Armstrong, 1992; Bossek et al., 1990; Larson et al., 1992; Chandra & Chakravorty, 1992). This is the result of the preferred 6-coordinate (octahedral) geometry of Mn(III) as well as a large number of other transition metals. However, octahedral complexes being coordinatively saturated are, in most cases, inherently less reactive. In this regard, a class of compounds that incorporate features to promote stability of high oxidation state metal ions, while maintaining reactivity, would be particularly advantageous for the catalysis selective of oxidation reactions with several organic substrates. These considerations provided the inventors with the motivation for the design and synthesis of improved ligand systems and metal complexes thereof such as those embodied by the present invention.

SUMMARY OF THE INVENTION

The present invention seeks to overcome the drawbacks inherent in the prior art by providing a novel ligand system for the stabilization of metals in high oxidation states to produce metal oxo centers that exhibit selectivity in the oxidation of organic substrates. These high oxidation state metal oxo complexes have electronic stabilization and steric features that protect terminal metal oxo centers and limit coordination numbers to less than six to promote reactivity.

In general terms, the PHAB ligand of the present invention can be defined by the following general structure:

Structure 1 wherein Y is a phenyl, substituted phenyl, biphenyl, substituted biphenyl including chiral binapthol, napthol, substituted napthol, alkyl and substituted alkyl; and X is separately or collectively a hydroxyl, amino, or thiol.

The substituents $R_1$–$R_4$ can include separately or collectively methyl, phenyl, t-butyl, neopentyl, trimethyl silyl and cyclohexyl.

An exemplary example of this ligand system is bis-amido bis alkoxo, 1,2-(bis-2,2-diphenyl-2-hydroxyethanamido) benzene referred to hereafter as $H_4$PHAB or PHAB when complexed with a metal. The ligand of the instant invention was designed to complex metals, prefererably transition metals.

The novel aspect of the foregoing structures is the fact that in the context of the present invention, the ligands are stabilizing for high oxidation states of metal ions and the R groups are substantially large to provide steric bulk and limit the coordination of the metal to less than 6. This novel tetradendate ligand system provides a unique electronic structure around the metal center to promote new reactivity. This ligand system can be used as a scaffold upon which more elaborate functionality is placed, allowing for control over the regioselectivity and stereoselectivity of reaction. Substitution of the R groups will produce changes in the steric bulk of the system and variation of the Y group in structure 1 will introduce modification to the size of the chelate ring formed by the metal, amido nitrogens, and the Y group. Functionalities such as chiral binapthol can be introduced at Y. Such changes in R and Y will provide regiochemical and stereochemical control over the catalyzed reaction. Substitution of the X group can provide increased stabilization for particular metal ions.

Certain particular embodiments of the invention relate to the PHAB ligands that are shown to form a novel five-coordinate $Mn^{III}$ dimer and to react with dioxygen to yield a $Mn^V$-oxo complex. The air oxidation of the $Mn^{III}$(PHAB) dimer proceeds in the absence of the ether solvent through a proposed autocatalytic path. The surprising reactivity of these five-coordinate PHAB complexes stabilized in the higher oxidation states allows new routes for hydroxylation, oxidation, epoxidation, oxo transfer, and enantioselective oxidation of organic substrates.

Exemplary organic substrates include alcohols, aldehydes, aldoses, alkylbenzenes, ketones, phenols, olefins, alkanes, ethers and thiols.

In further embodiments a wide variety of metals will be incorporated into the PHAB ligand system using the general synthetic protocol developed by the inventors for inserting metals, preferably transition metals, or any atom behaving as a metal such as iodine in its heptavalent state. Exemplary transition metals are Mn, Ru, Cr, Re, Fe and Tc. Other preferred metals will be those of the first transition series which have been shown to activate dioxygen or facilitate oxygen transfer to organic substrates.

In still further embodiments these pentacoordinate PHAB metal complexes will be used in the oxidation, hydroxylation, epoxidation, oxo transfer, and selective oxidation reactions of organic substrates. In the case of radioactive metals such as $Tc^{99}$, $Re^{188}$ and $Re^{186}$, these complexes may be used as agents in medical diagnostics.

Complexes containing radioactive isotopes are used as therapeutic agents and for detection purposes as a diagnostic aid. One such diagnostic technique is Single Photon Emission Computed Tomography (SPECT) which measures the biodistribution of the radioactive complex (Mazzi et al., 1991). Other applications for radioactive complexes will be apparent to those skilled in the art, such as those found in Remington, 1990; in particular, Chapter 33, pages 624–652, which are hereby incorporated by reference.

Paramagnetic metal complexes such as the Cr(V)-oxo and the Mn(III) dimer complex of the present invention can be used as imaging agents for techniques such as Magnetic Resonance Imaging (MRI).

The applications of novel paramagnetic metal complexes will be apparent to those of skill in the art as in U.S. Pat. No. 5,260,050, which is hereby incorporated by reference.

Some of the more stable metal oxo complexes, e.g., those containing chromium, manganese or ruthenium, are also contemplated for use as catalysts for the dismutation of superoxide and thus may have antieschemia properties. Such antioxidants have applications, e.g., in preventing tissue damage during surgery and heart attacks.

DEFINITIONS

Compound 1 is defined hereafter as the novel five-coordinate alkoxide bridged dimer $[Li\{Mn(PHAB)_2(1)\}]$ 4MeCN where $H_4PHAB$ is bis 1,2-(2,2-diphenyl-2-hydroxyethanamido)benzene Compound 2 is defined hereafter as $Ph_4P[Mn^V(O)(PHAB)]$ Compound 3 is defined hereafter as $Ph_4P[Cr^V(O)(PHAB)]$

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Absorbance at 410 nm monitoring the interconversion of 1 and 2 in THF upon the addition of air. The arrows indicate replenishment of air to the sealed cuvette. Reaction conditions were 0.37 mM 1 and 4.8 mM $Bu^n_4NClH_2O$ in THF at 50° C. A short lag period is observed, followed by rapid and nearly quantitative (>95%) conversion to 2. The lifetime of 2 is directly related to the availability of $O_2$. The two complexes were repeatedly interconverted by the addition of air and then sealing the system.

FIG. 5. Reaction of 1 with $O_2$ in THF yields two equivalents of $[Mn^V$-$(O)$ $(PHAB)]^-$(2) and 2-hydroxytetrahydrofuran (THF-OH). On the left is shown an ORTEP drawing of the core of $Li[Mn^{III}PHAB]_2^-$ for compound 1, showing the 50% thermal probability ellipsoids. Solvate molecules, hydrogen atoms, and phenyl groups are omitted for clarity. Selected bond distances (Å) and angles (deg) are as follows: Mn1-Mn2, 3.052(9); Mn1-O1, 1.904(5); Mn1-O2, 1.927(5); Mn1-N1, 1.914(6); Mn1-N2, 1.900(5); Mn1-O5, 2.174(5); Mn2-O5, 1.926(5); Mn2-O6, 1.981(5); Mn2-O2, 2.115(5); Mn2-N3, 1.911(6); Mn2-N4, 1.925(6); Li2-O1, 1.87(1); Li2-O6, 1.87(1); Mn1-O2-Mn2, 97.0(2); Mn1-O5-Mn2, 96.0(2); O2-Mn1-O5, 80.3(2); O2-Mn2-O5, 81.9(2); O1-Li2-O6, 113.0(7). On the right side is shown an ORTEP drawing of [Mnv(O) (PHAB)] anion of (2), showing the 50% thermal probability ellipsoids. Hydrogen atoms are omitted for clarity. Selected bond distances (Å) and angles (°) are as follows: Mn-O1, 1.558 (4); Mn-O2, 1.827(4); Mn-O3, 1.831(4); Mn-N1, 1.893(5); Mn-N2, 1.875(5); O1-Mn-O2, 110.0(2); O1-Mn-O3, 110.0 (2); O1-Mn-N1, 109.2(2); O1-Mn-N2, 108.5(2).

Anal. Calcd for $Ph_4P[Mn^v(O)(PHAB)]$, $C_{58}H_{44}N_2O_5P_1Mn_1$: C, 74.51; H, 4.74; N, 3.00. Found: C, 73.61; H, 4.75; N, 3.07. UV-vis(MeCN): $\lambda_{max}$ (nm) ($\epsilon$, cm$^{-1}$ M$^{-1}$) 414 (4020), 552 (993), 730 (415). From $Bu^n_4N[Mn$-$(O)(PHAB)]$, UV-vis (THF): $\lambda_{max}$(nm) ($\epsilon$, cm$^{-1}$ M$^{-1}$) 410 (3952), 558 (597), 730 (390).

Anal. Calcd for $Li_2[Mn^{III}(PHAB)]_2 \cdot 4MeCN$, $C_{76}H_{60}N_8O_8Li_2Mn_2$: Li, 1.04; Mn, 8.22. Found: Li, 0.99; Mn, 8.55 (Galbraith). Internally consistent C,H,N analyses were not obtained from eight determinations conducted by two laboratories (Oneida and Galbraith) on the same crystalline sample. Analysis of other crystalline samples of 1 gave similar results. UV-vis(THF): $\lambda_{max}$(nm) ($\epsilon$(per Mn), cm$^{-1}$ M$^{-1}$) 390 (749), 410 (728), 467 (707). A diffraction quality crystal of 1, taken directly from the mother liquor and coated with oil to prevent solvent loss, crystallized in the monoclinic space group $P2_1/c$, with a=13.42(4) Å, b=19.18

(7) Å, c=26.33(8) Å, β=99.69(2)°, V=6676 Å$^3$, $\rho_{calc}$=1.318 g cm$^{-3}$, and Z=4. Data collection at −120° C. for 2≦2θ≦46° provided 5381 reflections with I>3σ(I). The structure was solved by direct methods (SHELXS 86) and refined in TEXSAN 5.0 with anisotropic thermal parameters. Hydrogen atoms were calculated and fixed in the final refinements. The structure converged with a final R (R$_w$) value 0.061 (0.073) for 843 variables.

DETAILED DESCRIPTION OF THE PREFERRED EMBODIMENTS

Figure 1A:
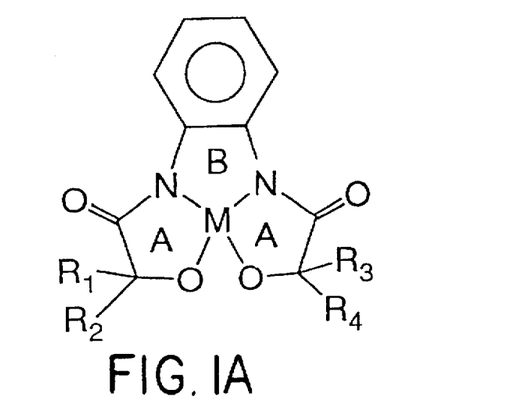
FIG. 1A. A generalized structure of the tetradentate ligand PHAB coordinated to a metal. Exemplary transition metals are Mn, Ru, Cr, Re, Fe and Tc. The substituents $R_1$–$R_4$ can include separately or collectively methyl, phenyl, t-butyl, neopentyl, trimethyl silyl and cyclohexyl. The figure shows the designation of the chelate rings as A and B for clarity.
Figure 1B:
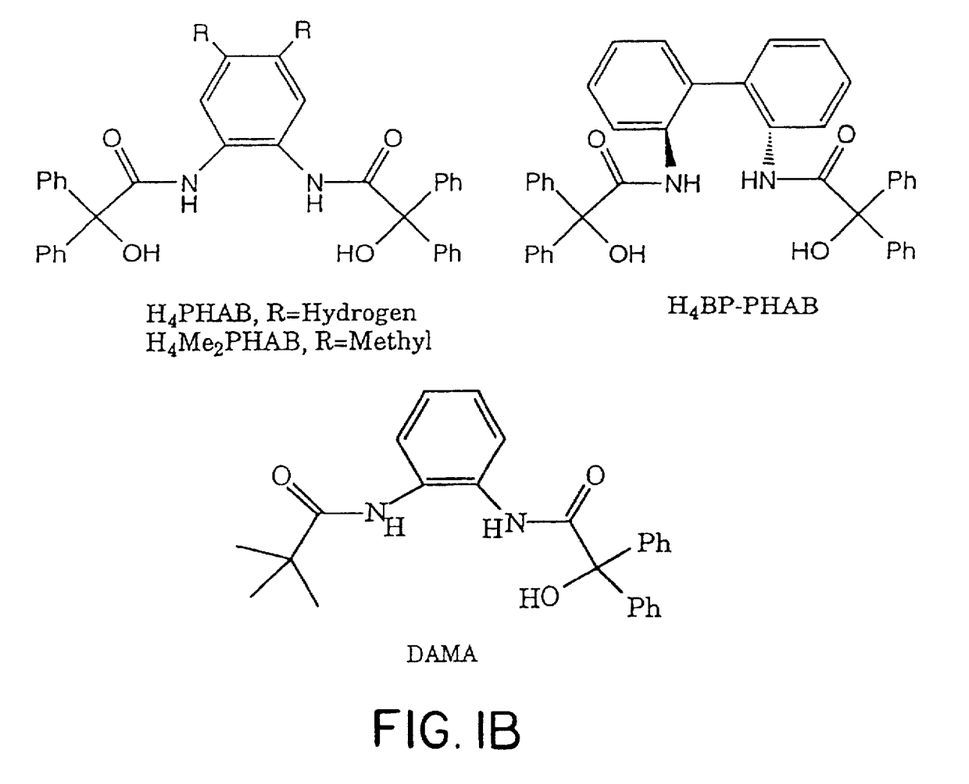
FIG. 1B. The tetradentate ligand $H_4PHAB$, dimethyl substituted ligand $H_4Me_2PHAB$, the biphenyl substituted ligand $H_4BP$-PHAB, and the tridentate ligand DAMA.
Figure 2A:
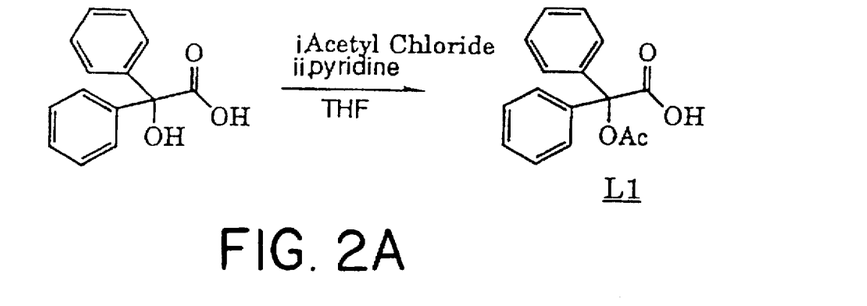
FIG. 2. Synthetic scheme for the $H_4PHAB$ ligand. The synthesis is accomplished in three steps as shown.
Figure 2B:
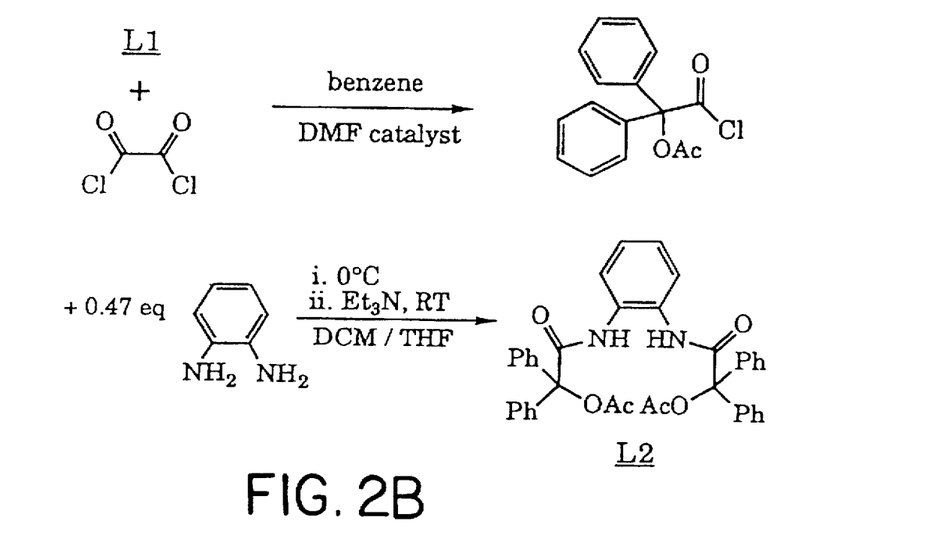
Figure 2C:
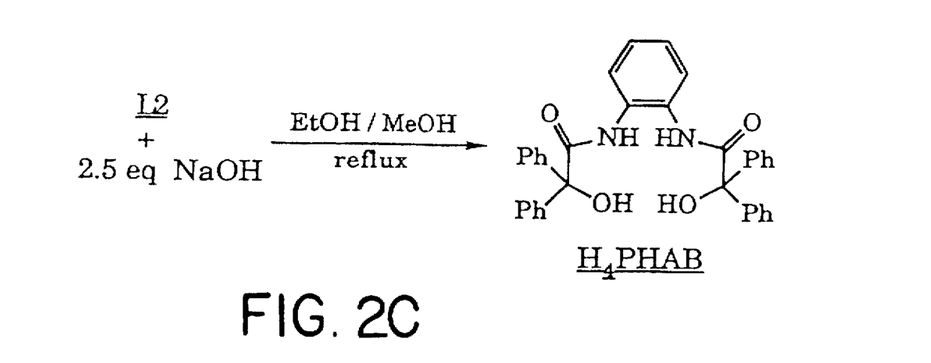

The inventors have synthesized and characterized a novel, sterically hindered chelating ligand system, PHAB and derivatives thereof (FIGS. 1 and 2). PHAB is shown to stabilize a number of metal compounds in high oxidation states, in particular those compounds containing terminal oxo ligands (MacDonnell et al., 1994). The PHAB ligand imparts a lipophilic and anionic character to metal complexes. The PHAB ligand and its metal complexes are novel compositions of matter that exhibit unique properties and reactivity. The oxidation reactions that the PHAB metal complex catalyze are of potential commercial importance in the petroleum, specialty chemicals and pharmaceuticals industries. Radioactive technecium and rhenium complexes of this ligand are contemplated to have applications as radiochemical imaging agents in humans. The radioactive isotopes Tc$^{99}$, Re$^{186}$ and Re$^{188}$ can be used as radio imaging agents. Tc$_m^{99}$ is a high energy gamma emitter while Re is less energetic, and therefore less damaging, beta emitter. The use of these metals as radio imaging agents has been previously reported (Mazzi et al., 1990). Paramagnetic compounds such as the Cr(v)-oxo compound, can be used in medical diagnostic techniques such as Magnetic Resonance Imaging (MRI). Other paramagnetic metal complexes such as those of the lanthanide series, are also envisioned by the inventors.

Some of the more stable metal oxo complexes, e.g., those containing chromium, manganese or ruthenium, are also contemplated for use as catalysts for the dismutation of superoxide and thus may have antieschemia properties. Such antioxidants have applications, e.g., in preventing tissue damage during surgery and heart attacks.

Figure 3A:
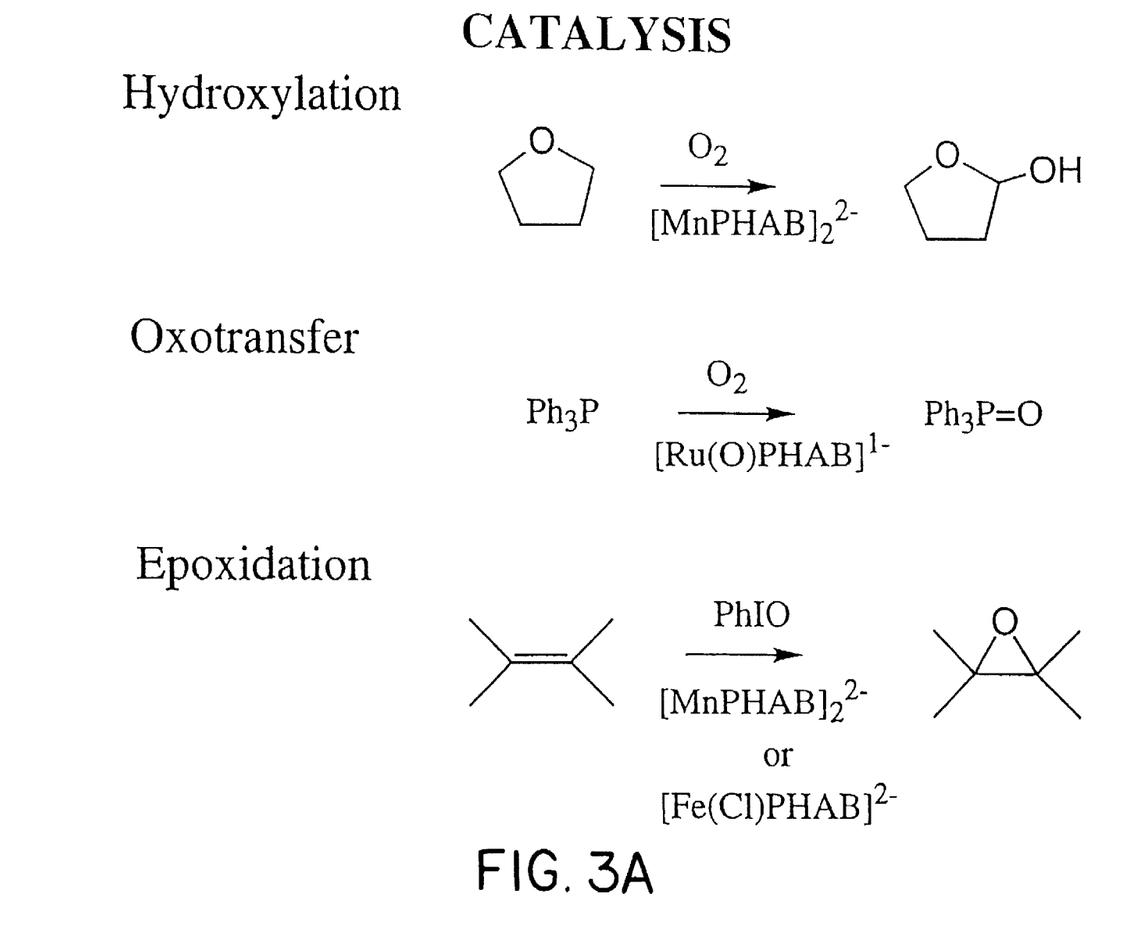
FIG. 3A. Reactions catalyzed by metal oxo complexes of the tetradentate ligand PHAB. Reactions catalyzed include hydroxylation, oxo transfer, and epoxidation of an olefin.
Figure 3B:
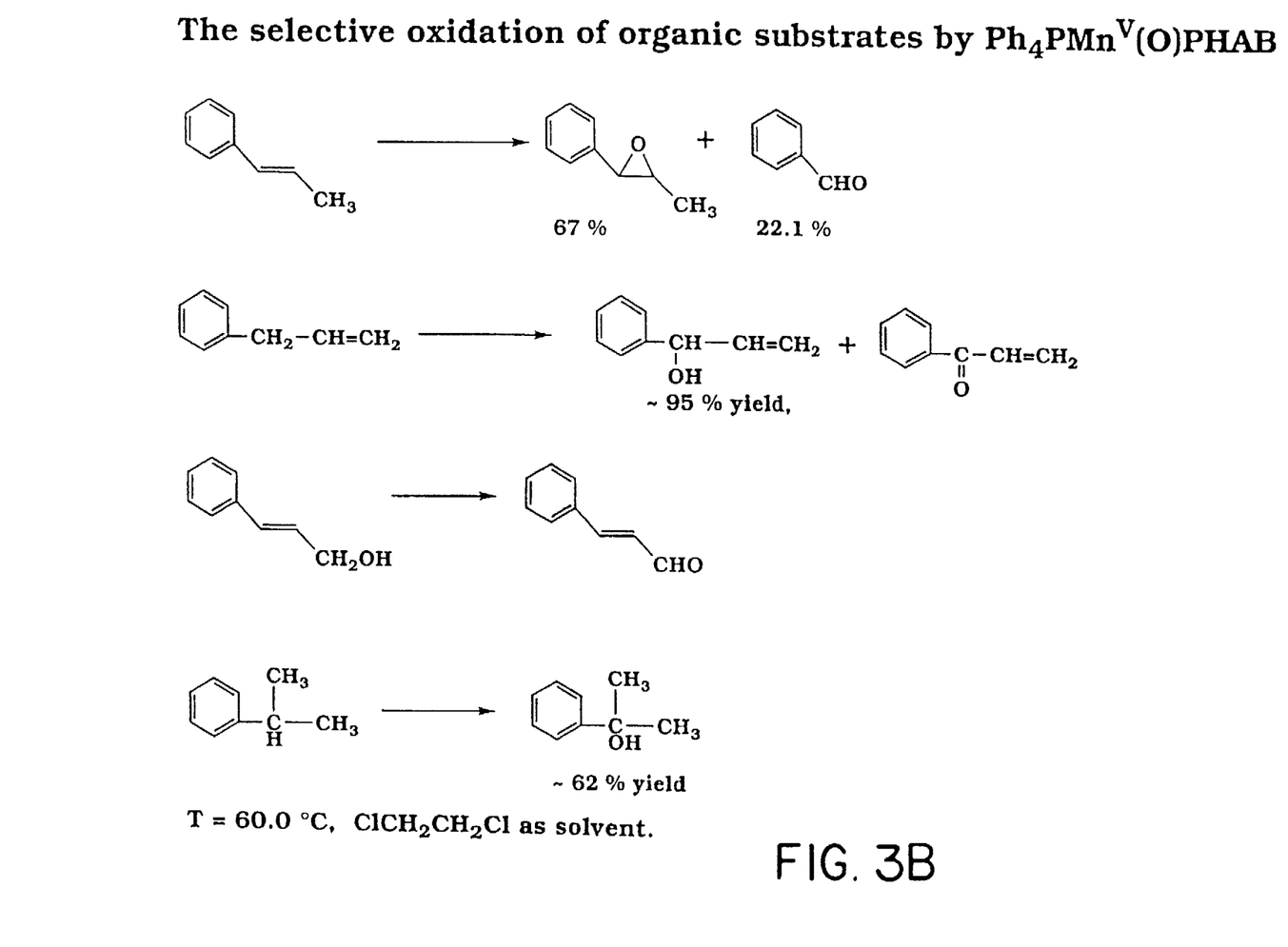
FIG. 3B. Selective oxidation of organic substrates by $Ph_4PMn^V(O)$ PHAB.

The inventors have demonstrated that certain of the PHAB complexes can serve as catalysts for the air oxidation of a variety of organic substrates. Epoxidation at olefins, alkane hydroxylation, and allylic oxidation processes are demonstrated, as are C-H Activation processes as shown in FIG. 3. The ligand is a novel composition of matter, as are the completely characterized complexes of the following metals Cr(V)O, Mn(III), Mn(V)O, Ru(V)O, Ru(VI)O, Re(V)O, and Fe(III)Cl.

The design of this novel ligand system incorporates several features important in stabilizing high oxidation state complexes. The first feature, the pendant phenyl groups, favors five coordinate complexes. This steric bulk prevents octahedral coordination and, to date, A oxo-bridge formation. A second feature of these chelating ligands is the presence of strong bases such as amidate nitrogens and alkoxide oxygens. Another aspect of this robust tetradentate ligand is the absence of beta hydrogens that would otherwise leave the ligand sensitive to internal redox decomposition mechanisms. Finally, macrocyclic designs have been avoided, allowing some conformational flexibility in the local coordination environment. The new chelating ligand of the invention, PHAB, exhibits these properties. Preliminary physical, spectroscopic and catalytic results for the PHAB complexes are discussed herein.

Structures for complexes of (Cr(V)-oxo and Mn(V)-oxo) have been reported by Collins and coworkers although no data on their reactivity have been reported. The most notable difference of the Collins structure (Collins et al., 1986 patent) is the extra carbon in each A ring (FIG. 1A). This combined with the planar phenyl groups as part of the backbone of the ring does not afford close attachment of bulky substituents for protection of the reactive metal oxo center. This has an effect on the overall stability of the catalyst as well as limits the amount of stereo selectivity possible. (Jacobsen et al., 1991, Lee et al., 1991). This is most clearly evidenced by the novel reactivity patterns of the [M(O)PHAB] complex.

Jacobsen et al. (1991) have also reported ligand systems to stabilize metal oxo complexes. However, the ligands used in those systems are a Schiffs base (—N═R). This changes the charge of the ligand, when the metal is inserted, to two less than the system of the present invention. Such a change certainly effects the stability of the metal oxo, resulting in very different reactivity and selectivity.

Considering periodic trends among the transition metals and the general structural requirements of d$^1$, d$^2$, d$^3$, d$^4$ and d$^5$ metal center demonstrated to form complexes to the PHAB ligand, the inventors contemplate that the ligand will form complexes with a wide range of metals. The inventors have developed general synthetic protocol for inserting metals and can predict that the fundamental square pyramidal metal oxo environment will be preserved for d$^1$ and d$^2$ complexes while more distorted trigonal bipyramidal species (such as seen in the Ru(V)O structure) are expected for d$^3$ complexes. The synthetic structural and kinetic studies described herein allow the prediction of the influence of the d manifold electron distribution on the reactivity of the metal oxo group and outcome of oxo transfer reactions to organic substrates.

The d$^2$ [PHABMn$^V$O]$^-$ anion can be synthesized via several routes with various counter ions. The d$^1$ Cr(V)-oxo complex is isostructural with the Mn(V)-oxo, but the former exhibits significantly longer M-O$_{oxo}$ distances than the latter. The electronic origin of this bond lengthening on going from d$^1$ to d$^2$ is unknown. The Mn(V) complex is diamagnetic as expected for a d$^2$ oxo complex in a square pyramidal ligand field while the d$^1$ Cr(V)-oxo is paramagnetic (g=1.987; $^{14}$Na$_n$=2.62 G).

The Mn(V)-oxo complex will transfer the oxo atom to PPh$_3$ with a second order rate constant of 27 M$^{-1}$ sec$^{-1}$, whereas the Cr(V)-oxo compound is unreactive even at elevated temperature and extended times. Olefins and alcohols react in a parallel manner. Stoichiometric reactions of a variety of organic substrates with the Mn(V)-oxo complex are observed, including hydroxylation of THF to give 2-hydroxytetrahydrofuran with a second-order rate constant of 1.8×10$^{-4}$ M$^{-1}$ sec$^{-1}$ at 50° C. and a deuterium isotope effect of 10.3.

Figure 4:
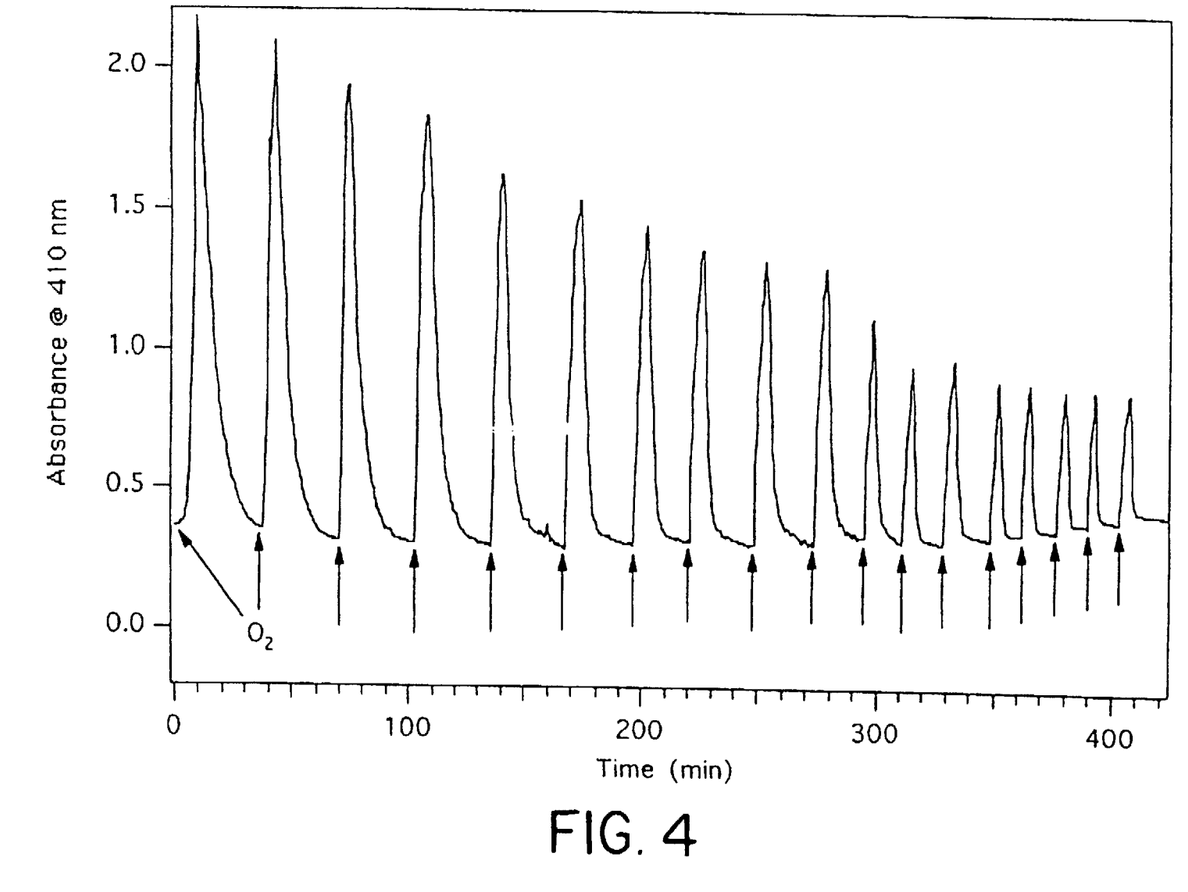
Figure 5:
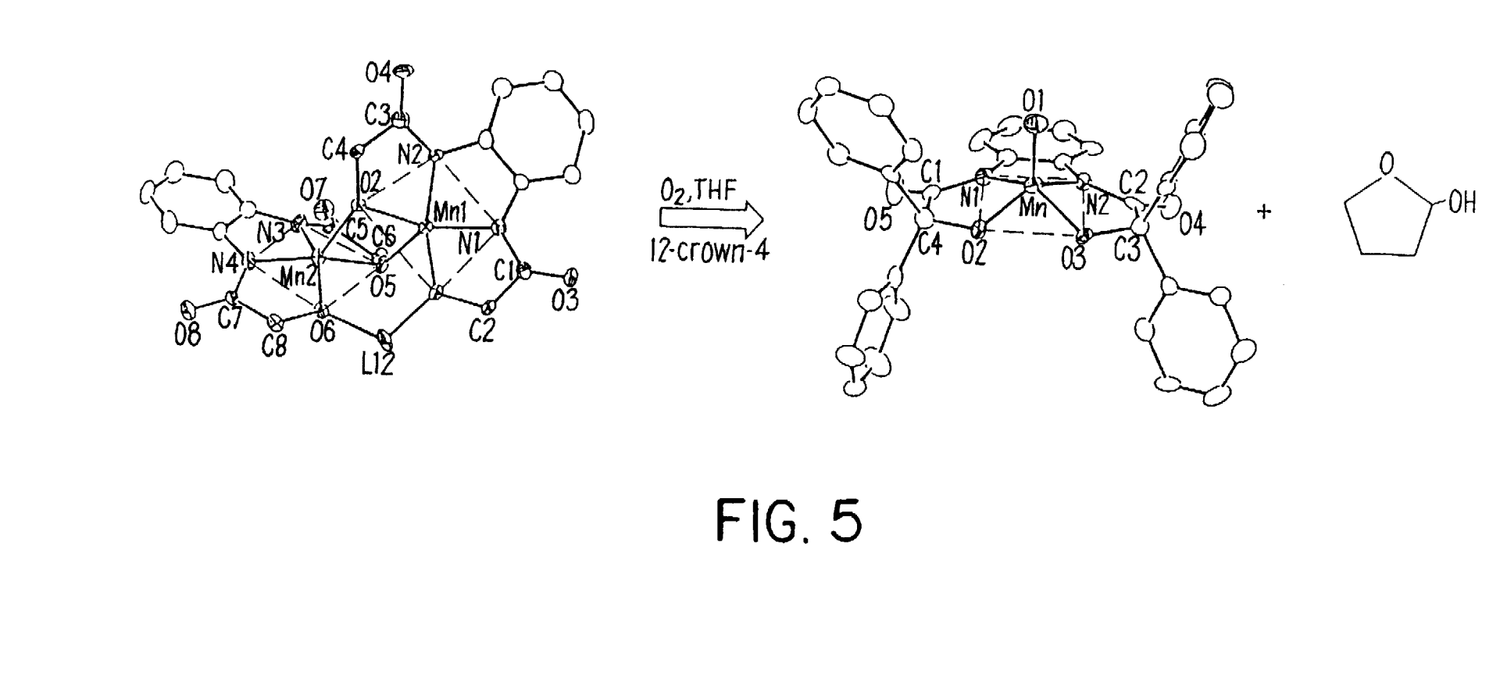
Figure 6:
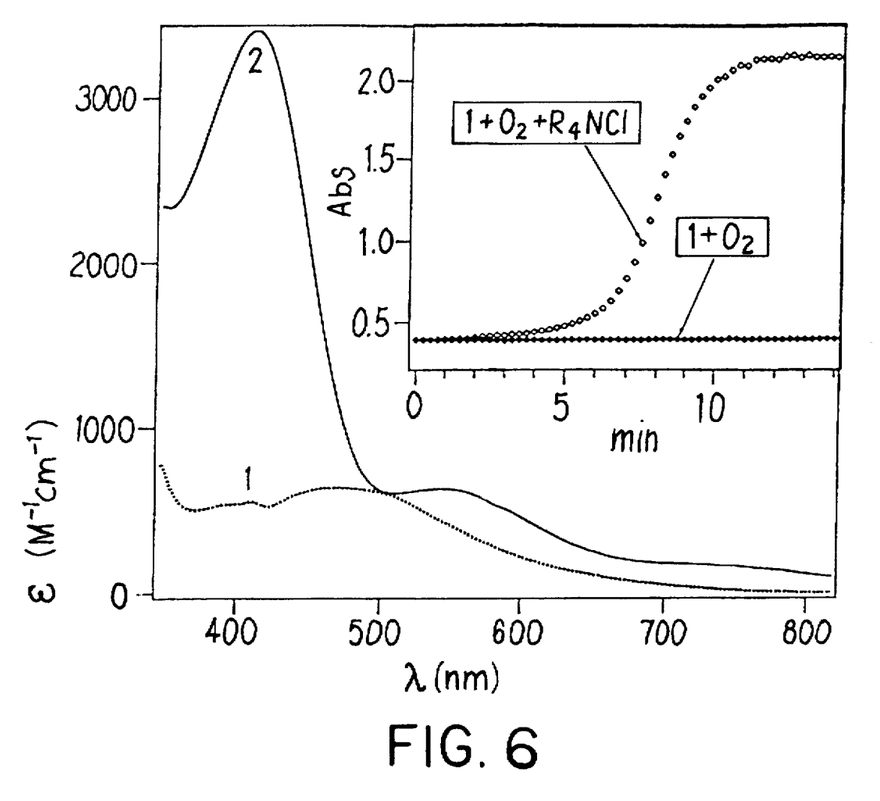
FIG. 6. Absorbance spectra of the red Li$_2$[Mn$^{III}$(PHAB)]$_2$·4MeCN (1) in THF (freshly distilled from sodium/benzophenone) before and after admission of air to form 2 equivalent of green [Mn$^V$(O)L]$^-$(2). Inset: absorbance at 410 nm was recorded at 15 second intervals after addition of air to a THF solution of 1 (0.54 mM) in 10 mM Bu$^n_4$NCl, thermostated at 50° C.

Under anaerobic conditions THF solutions of the emerald green color of the Mn(V)-oxo complex fade to a burgundy-color characteristic of the Mn(III) dimer. Introduction of a limited quantity of dioxygen or air will restore the color of the metal oxo complex, which will fade again until additional $O_2$ is added as shown in FIG. 4. Each cycle of air oxidation is accompanied by a burst of substrate oxidation and at longer times the lactone is observed as a secondary oxidation product. A turnover number of 50 $hr^{-1}$ was observed. These observations indicate that Mn(V)-oxo complex can catalyze the air oxidation of THF to yield the mono hydroxylated product. The Mn(III) dimer could also catalyze the air oxidation of THF in the absence of added reductants only upon chelation of the bridging lithium cation by a crown ether as shown in FIG. 5 or tetraalkylammonium chloride ($R_4NCl^-$) as shown in FIG. 6. Mn(III) dimers crystallized in the absence of lithium react, after a short lag period with THF in $O_2$ saturated solutions with out the addition of crown ethers. Other simple Mn(II) and (III) salts would not catalyze the reaction and a role for hydroperoxides contaminating the THF was ruled out.

Anaerobic crystallization of the burgundy solution containing low valent Mn PHAB complexes provided insight to the nature of the manganese precursor that reacts with $O_2$, $ClO^-$, PhIO or tBuOOH to give Mn(V). Instead of a mononuclear, square planar Mn(III) complex an alkoxide bridged and lithium-bridged dimer was obtained. Each Mn is five coordinate and exhibits a long axial interactions with the bridging alkoxide.

Since Mn(V) reacts with PPh3 and since the Mn(III) is oxidized by t-BuOO-, it is estimated that the $Mn^V$-O bond strength lies between the P-O and tBuO-O bond strengths or between 40 and 133 kcal/mol, while the $Cr^V$-O bond strength is likely greater than 133 kcal/mol.

Several $d^1$ and $d^2$ first row transition metal complexes with a single terminal oxo ligand have been structurally characterized. In these cases, the d-electrons typically occupy a non-bonding molecular orbital. For $d^3$ metal oxo centers in a square pyramidal ligand field, the additional electron typically occupies a molecular orbital with significant metal oxo antibonding character. Comparison of the Ru(VI)-oxo ($d^2$) and Ru(V)-oxo ($d^3$) structures above suggests that the primary coordination sphere undergoes a significant distortion of the ligand amide groups to trigonal bipyramidal structure upon the addition of a third electron to the d-manifold. As expected, the strongly sigma-donating oxo group occupies an equatorial site. Based on vibrational and structural data the metal oxo bond order has diminished relative to the $d^2$ system, but it is possible that the HOMO for this trigonal bipyramidal (TBP) ligand field has less metal oxo antibonding character than the HOMO for a square pyramidal $d^3$ complex. The kinetically inert nature of the geometrically distorted complex allows for the production of a chiral species, the isolation of which, will allow for enatioselective reactions. In spite of the amide distortion penalty, the TBP arrangement with an equatorial oxo group is preferred. A similar geometry may allow some stabilization of iron centers in oxygenase enzymes.

As envisioned by the inventors, the combined steric and electronic features of the PHAB environment stabilize metal oxo moieties to different extents, depending upon d orbital occupancy.

The inventors have demonstrated the use of PHAB metal oxo complexes in selective oxidation, oxo transfer, and epoxidation reactions as set forth in the Examples. The incorporation of paramagnetic and radioactive metals will allow for the use of these complexes in medical diagnostics imaging agents.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

THF was reagent grade (Fisher) and was dried via published procedures before use unless otherwise noted. Acetonitrile, benzene, $CHCl_3$, pyridine and diethyl ether were all reagent grade (Fisher). All other regents were purchased from Aldrich Chemical Company, Milwaukee, Wis. and used as received. Other common solvents were analytical reagent grade and used as received.

All UV/vis spectra were measured on an HP 8452A Diode Array Spectrophotometer interfaced with a PC using HP 89531A operating software. Infrared data were obtained on a Mattson Alpha Centauri FT-IR spectrophotometer. FAB-MS was performed at the ASL of Northwestern University. Elemental analysis was performed by Oneida Labs in Whitesboro, N.Y. NMR spectroscopy was performed on a Varian Gemini 300 NMR.

EXAMPLE 1

SYNTHESIS OF $H_4$PHAB AND DERIVATIVES

A. Synthesis of Bis 1,2-(2,2-Dyphenyl-2-Hydroxyethanamido) Benzene ($H_4$PHAB)

The ligand was prepared in a three step synthesis described below:

Acetylbenzilic Acid (L1)

Acetyl chloride (35 mL, 490 mmol) was added dropwise to a solution of benzilic acid (100 g, 438 mmol) in 300 mL THF over a period of five minutes. The solution was cooled to 0° C. and pyridine (70 mL, 865 mmol) was added dropwise over a period of 30 minutes, during which time a thick white precipitate developed. The ice bath was removed, the reaction flask was equipped with a $CaCl_2$ drying tube and stirred overnight. The next day, the solution was filtered to isolate a white precipitate and the yellow THF supernatant was concentrated to a turbid oil. Most of the product was isolated in the precipitate as the pyridinium acetylbenzilate salt, but some was retained in the supernatant. The precipitate and oil were added to a large separatory funnel charged with 1000 mL diethyl ether and 400 mL of 1.2M HCl. The contents were thoroughly mixed, the aqueous portion separated and discarded. The ether solution was washed twice with 400 mL 1.2M HCl, once with 300 mL saturated NaCl solution, dried over $MgSO_4$, filtered and concentrated to approximately 200 mL. The product was precipitated by addition of 800 mL hexanes, isolated by filtration, and air dried overnight. Yield 88 g (74%). $^1$H NMR ($CDCl_3$): δ7.1–7.7 (m, 10H ArH), 5.7 (s, 3H, COOH), 2.08 (s, 3H, RO(O)$CCH_3$). This synthesis could be easily modified by one of skill in the art to incorporate a thiol or amino analog of benzylic acid.

Synthesis of Acetate protected PHAB (L2)

The acid chloride of L1 was generated by dropwise addition of oxalyl chloride (17 mLs, 195 mmol) to a stirred, ice cold suspension of L1 (30 g, 111 mmol) in 225 mL of benzene and 5 drops of DMF. Once all the oxalyl chloride was added, the reaction was warmed to room temperature and stirred for one hour. After gas evolution ceased, the resulting clear benzene solution was concentrated in vacuo to give a thick oil. The oil was washed by addition of 50 mL CH$_2$Cl$_2$, then concentrated and dried in vacuo for 1 hour. The resulting acid chloride was dissolved in 75 mL CH$_2$Cl$_2$ and 200 mL THF. 1,2-phenylenediamine (5.1 g, 53 mmol) in 40 mL THF was added dropwise over a 10 min period to the acid chloride solution during which a white precipitate forms. The reaction flask was cooled in an ice water bath and triethylamine (39 mL, 227 mmol, Mallinckrodt) was added dropwise over a 30 min period. The flask was equipped with a CaCl$_2$ drying tube and stirred while slowly warming to room temperature overnight. The solution was filtered to remove the triethylammonium chloride salt and concentrated to an oil. The oil was dissolved in 200 mLs diethyl ether and filtered through a pad of silica (enough to fill a 60 mL glass frit). An additional 100 mL diethyl ether was used to rinse the silica pad and the combined supernatants were concentrated to ~50 mL. The product crystallized from solution upon standing overnight. The crystalline product was collected by filtration, washed with 50 mL cold diethyl ether, and air dried for 6 hr. Yield 13.6 g (48%). $^1$H NMR(CDCl$_3$): δ8.82 (s,2H, NH), 7.2–7.6 (m, 24H, ArH), 2.02 (s,6H, OOCCH$_3$).

Bis 1,2-(2,2-diphenyl-2-hydroxyethanamido)benzene (H$_4$PHAB)

To a solution of L2 (8.0 g, 13 mmol) in 100 mL MeOH and 25 mLs EtOH was added 2.5 g of finely ground NaOH (63 mmol). The resulting slurry was refluxed for 4 hrs during which the solution turned clear. The solution was then cooled to room temperature and quenched by addition of 150 mL 1.5M HCl. This solution was extracted once with 300 mL CHCl$_3$ and a second time with 100 mL CHCl$_3$. The combined organic portions were dried with MgSO$_4$ filtered and concentrated to approximately 100 mL. The crude product was precipitated by slowly pouring the CHCl$_3$ solution into 1600 mL hexane and isolated by filtration. The off-white solid was extracted with 800 mL diethyl ether, concentrated to 200 mLs and left to crystallize overnight. The resulting white crystalline solid was filtered, washed with 20 mL cold diethyl ether, and dried in vacuo at 78° C. for 3 hrs. Yield of first crop 3.7 g (54%), subsequent crops bring the total yield to 83%. Analysis calculated for C$_{34}$H$_{28}$N$_2$O$_4$: C,77.25;H,5.34;N,5.30. Found: C,77.27;H, 5.31;N,5.47. $^1$H NMR (d$_6$-DMSO) :δ10.12 (s,2H, NH), 7.1–7.6 (m,12H, ArH),3.33 (s,2–3 H, OH). Mass spectroscopy (FABS): nominal molecular weight calculated 528; nominal molecular weight found 528. IR (KBr): "amide CO=1668 cm$^{-1}$.

B. Dimethyl Substituted Ligand (Me$_2$H$_4$PHAB)

This synthesis was a simple modification of the H$_4$PHAB synthesis, substituting the appropriate amount of 4,5-dimethyl-1,2-phenylenediamine in place of the phenylenediamine. [Yield 60%; Elemental analysis for C$_{36}$H$_{32}$O$_4$N$_2$ found(calc*): C, 72.62(72.96); H, 5.74(6.12);N, 4.56(4.72); FABS anion calculated nominal molecular weight/charge 555, found 555; IR of KBr pellet (amide cm$^{-1}$) 1673, 1590,1530; $^1$H NMR (δvs. d$_6$DMSO) 9.98 (s,2H,NH), 7.2–7.5 (m,20H,ArH),7.07 (s,2H, backboneH), 3.4 (s, 2H, OH), 2.2 (s, 6H, CH$_3$)]. *Calculated includes two water molecules per ligand, indicating drying this species at high temperatures was needed to fully remove the water(s) of hydration.

C. Synthesis of H$_4$BP-PHAB

The synthesis was analogous to the original H$_4$PHAB synthesis, except biphenyl diamine was substituted for the phenylene diamine in the coupling step. The deprotected ligand was precipitated from an ethanol solution cooled to −10° C. [Yield based on benzilic acid starting material: 13.8%;$^1$H-NMR (δvs. d$_6$-DMSO) 9.47 ppm (s, 1H, NH); 7–8 ppm (m, 14H, ARH); 3.35 ppm (s, 1H, OH); Positive ion FABS-Mass Spectrum expected parent peak at 605, found 605; IR of a KBr pellet, amide carbonyl at 1670 cm$^{-1}$].

D. Synthesis of DAMA

Step 1: The acetate protected acetylbenzilic acid (acid chloride) was made as described in the synthesis of H$_4$PHAB. This compound was isolated as a yellow oil from benzene, redissolved in tetrahydrofuran, and added dropwise to an excess of 1,2-phenylenediamine (1.5 eq) in ice-cooled tetrahydrofuran. After addition of the diamine, 30 mL of triethylamine (TEA) was added and the resulting solution warmed to room temperature. The following day the solution was filtered to remove the TEA hydrochloride precipitate, leaving a red/yellow tetrahydrofuran solution. The tetrahydrofuran was removed by rotary evaporation and the residue was redissolved in a minimum of dichloromethane (DCM). Slow evaporation of the DCM solvent yielded a microcrystalline product (NF2265A). [$^1$H-NMR (δvs. d$_6$-DMSO) 9.47 ppm (s, 1H, NH); 7–8 ppm (m, 14H, ArH); 4.56 ppm (s, 2H, NH$_2$); 2.25 ppm (s, 9H, CH$_3$)].

Step 2: 1.5 equivalents of trimethylacetylchloride (Aldrich) was added dropwise to the product from step 1 dissolved in 100 mL of tetrahydrofuran and cooled in an ice bath. To this solution was added 1.5 equivalents of TEA. The solution was stirred a total of 4 hours. Filtration to remove the TEA hydrochloride revealed a translucent yellow solution. The tetrahydrofuran was removed under reduced pressure and the resulting residue precipitated with hexanes. Washing with diethyl ether left a white precipitate (NF2267). [$^1$H-NMR, (δvs. d$_6$-DMSO) 9.57 ppm (s, 1H, NH); 9.12 ppm (s, 1H, NH); 7–7.7 ppm (m, 14H, ArH); 3.35 ppm (H$_2$O); 2.28 ppm (s, 3H, CH$_3$); 1.14 ppm (s, 9H, CH$_3$)].

Step 3: Removal of the acetate protecting group was accomplished in the usual manner of base hydrolysis (reflux ligand over 4 hours in a 3:1 methanol/ethanol mixture with 1.2 equivalents of sodium hydroxide). Extraction of the final product with chloroform afforded a white precipitate upon addition of diethyl ether and hexane. The powder was recrystallized by cooling a saturated dichloromethane solution to −4° C., yielding clear needles. [$^1$H-NMR (δvs. d$_6$-DMSO); 9.77 ppm (s, 1H, NH); TMA amide 9.25 ppm (s, 1H, NH);7–8 ppm (m, 14H, ArH); 3.34 ppm (s, 1H, OH); 1.17 ppm (s, 9H, cH$_3$); Mass Spectrum (positive ion FAB), peaks at 403 (monomer) and 806 (dimer); IR (KBr pellet); amide carbonyls at 1692 and 1636 cm$^{-1}$; elemental analysis, theoretical (found); C, 74.60 (74.49); H, 6.51 (6.66); N 6.96 (6.94); melting range 189°–191° C.].

EXAMPLE II

SYNTHESIS OF Li$_2$[Mn(PHAB)]$_2$ COMPOUND (1)

The dimeric structure of Li$_2$[Mn(PHAB)]$_2$ (1)4MeCN is shown in FIG. 5 and further described in the text accompanying FIG. 5. The alkoxo bridging motifs are similar to those found in other Mn$^{III}$ dimers (Garcia-Deibe et al., 1991; Larson & Pecoraro, 1991; Yu et al., 1991; Vincent et al., 1986; Nishida et al., 1988). However, the four phenyl groups restrict both Mn$^{III}$ centers to a five-coordinate alkoxo-bridged geometry which is unprecedented in the rich chemistry of manganese dimers (Larson et al., 1992). A second distinct bridging interaction is formed by a lithium ion which is tightly bound between two terminal alkoxides. The lithium cation was not metathesized during the crystallization of 1 in the presence of 0.1M KPF$_4$.

The following synthetic method was used for Li$_2$ [MnPhBABO]$_2$ (1) 4MeCN.

Addition of anhydrous $MnCl_2$ (0.29 g, 2.34 mmols) to a solution of $H_4PHAB$ (1.0 g, 1.89 mmol) and LiOMe (0.294 g, 7.75 mmol) in 90 mL MeOH and dry air give a light red solution which rapidly darkens to a deep maroon red color. Filtration and rotary evaporation yielded a red solid, which is further purified by silica chromatography with THF eluent. The first yellow band was discarded while the second deep purple-red band was collected and concentrated to approximately 10 mL and precipitated with diethyl ether. The dark red solid was recrystallized from diethyl ether layered acetonitrile solution (0.1M in $KPF_6$). Yield 0.83 g (65.8% based on ligand).

EXAMPLE III

SYNTHESIS OF $Ph_4P[Mn(O)PHAB]$ COMPOUND (2)

When lithium complexing agents are added, facile oxidation of 1 occurs in air or $O_2$-saturated, peroxide-free THF, yielding $[Mn^V(O)(PHAB)]^-$ (2) and 2-hydroxytetrahydrofuran (THF-OH). The oxomanganese (V) complex, 2, has been isolated and structurally characterized as follows:

The $Mn^{III}$ dimer $Li_2[Mn^{III}PHAB]_2$ (1)4MeCN (1) (300 mg, 0.23 mmol) was dissolved in 25 mL $CH_2Cl_2$ and 5 mL MeCN to form a deep red-brown solution. The solution was cooled to 0° C. and iodosylbenzene (200 mg, 0.94 mmol) added. After stirring for 30 minutes, the solution becomes a deep green-brown color. The solution was filtered, concentrated to approximately 3 mLs and the product precipitated with 50 mLs diethylether and 20 mLs pentane. Metathesis with $Ph_4P.Cl$ (200 mg, 0.53 mmol) in 10 mL $CH_2Cl_2$, filtering, and slowly layering the solution with 30 mL diethylether gave dark crystals. Yield 241 mg (55%).

As outlined in this example, dark crystals of 2 are grown by layering diethyl ether onto a solution of 1 and $Ph_4PCl$ in dichloromethane in the presences of air. 2 crystallizes in the monoclinic space group $P2_1/n$, with a=19.156(3) Å, b=11.842(4) Å, c=20.025(3) Å, β=92.48(1)°, V=4538 Å$^3$, $\rho_{calc}$=1.368 g cm$^{-3}$, and Z=4. Data collection at −120° C. from $2 \leq 2\theta \leq 46°$ provided 3410 reflections with $I > 3\sigma(I)$. The structure was solved by direct methods. (SHELXS 86) and refined in TEXSAN 5.0 with 485 variables to final $R(R_w)$ values 0.052 (0.052).

The above structural characterization (FIG. 5) reveals the oxomanganese (V) complex, 2, as a square-pyramidal $Mn^V$ with a terminal oxo bond distance of 1.558(4) Å, in good agreement with the values obtained for the two other structurally characterized oxomanganese (V) complexes (Collins & Gordon-Wylie, 1989; Anson et al., 1987; Collins et al., 1990; Workman et al., 1992).

Conversion of 1 to 2, monitored as a change in the visible spectrum at 410 nm (FIG. 6), will not occur unless a lithium-specific chelator, such as excess 12-crown-4 (distilled from NaH under nitrogen immediately prior to use to eliminate possible contaminating peroxides) or tetraalkylammonium chloride ($R_4NCl$), is added. Furthermore, the lithium-free dimer $(Bu^n_4N_2)[Mn(PHAB)]_2$ (3) reacts with dioxygen to form 2 in the absence of $R_4NCl$ or 12-crown-4. Apparently, loss of the $Li^+$ bridge leads to formation of an $O_2$-reactive species. The latter could be a dimer in an altered conformation or a dissociation product of 1, such as a four-coordinate $Mn^{III}$ monomer. Note, Anal. Calcd for $(Bu^n_4N)_3[Mn(PHAB)]_2$ (3), $C_{100}H_{120}N_6O_8Mn_2$: C, 73.06.; H, 7.36; N, 5.11. Found: C, 73.06; H, 6.94; N, 5.13.

The reaction of 1 with $O_2$ in the presence of $Bu^n_4NCl$ (FIG. 2), inset) commences after an induction period of approximately 4–6 min, and complete conversion of 1 to 2 requires a total of ca. 10 min at 50° C. A GC-MS analysis of the reaction mixture at this point revealed formation of 2–3 equivalent of THF-OF per $Mn^{III}$. The observation of an induction period and a decreasing half-life for formation of 2 are characteristic of an autocatalytic process (Steinfeld et al., 1989). The inventors propose that a $Mn^{III}(O_2)$ or $Mn^{iv}(O_2^-)$ intermediate initiates THF autoxidation by H atom abstraction. The resulting THF radicals could react with $O_2$ to ultimately give 2-tetrahydrofuran hydroperoxide (THF-OOH), which is expected to rapidly react with 1 to form 2 and THF-OH. The excess of THF-OH over $Mn^{III}$ indicates that other reactions may yield THF-OH, such as the direct reaction of 2 with THF. In support of this model, it was found that addition of exogenous alkyl hydroperoxides causes an immediate conversion of 1 to 2 even without lithium complexing reagents at 50° C. In addition, hydroperoxides are known to generate oxomanganese(V) complexes in related systems (Collins & Gordon-Wylie, 1989).

Other $O_2$ activation steps, such as initiation of THF autoxidation by trace contaminating $Mn^{II}$ or $Mn^{III}$ species or by residual THF-OOH in the neat solvent, are unlikely as neat solutions of 1 are stable in the presence of $O_2$ until $R_4NCl$ or 12-crown-4 is added. Control experiments demonstrate that 2 does not require the presence of lithium complexing agents to initiate autoxidation of 1. Thus contamination of solid samples of 1 by 2 cannot be responsible for initiating the overall reaction shown in FIG. 1. Furthermore, when 1 is replaced by $Mn(acac)_2$, $MnCl_2$, $Mn-(OAc)_2$, $Mn(OAc)_2$, or $Mn^{II}$ (salophen, an abbreviation for the Schiff base of o-phenylenediamine and salicylaldehyde), no $O_2$ oxidation of the metal centers or THF is observed by GC at 50° C. over a 2-h period. While reduction of $Mn^{III}$ complexes in other ligand fields can occur in THF (Anderson & Kochi, 1970), an initiation step in which 1 is reduced to a $Mn^{II}$ species is unlikely for these PHAB complexes. The extreme stability of the dimeric $Mn^{III}$ centers of 1 and 3 with respect to reduction is clear in cyclic voltametry studies: neither 1 nor 3 is reduced electrochemically upon scanning to −2.0 V vs SCE in acetonitrile. Cyclic voltametry of 1 or 3 shows two reversible redox processes, consistent with one-electron oxidations of 1 to give the $Mn^{III}M^{IV}$ dimer (standard reduction potential (ur SCE), $E_{1/2}$=0/73 V) and subsequently the $Mn^{IV}Mn^{IV}$ dimer ($E_{1/2}$=1.19 V). Conditions: 2 mM and 0.1M $Bu^n_4NPF_6$ in MeCN; scan rate, 100 MV/s; glassy carbon electrode.

Under anaerobic conditions, the oxygen atom of 2 can be transferred to a variety of substrates, including phosphines, ethers, and olefins. For instance, the reaction of this $Mn^V$-oxo complex with norbornylene gave norbornylene epoxide in 11% yield. A solution of 0.060 mmol of $Bu^n_4N[Mn(O)(PHAB)]$, 0.060 mmol of bromobenzene (internal standard), and 0.545 mmol of norbornylene in 0.5 mL of 1,2-dichloroethane was degassed by three freeze-thaw cycles and placed under a $N_2$ atmosphere. This solution was heated to 50° C. for 2 h and then analyzed GC. The only major product was identified as norbornylene epoxide by coinjection with the authentic material. A total of yield of 0.007 mmol or norbornylene epoxide (11%) was found. The inventors propose to coupling the oxidation of 1 to 2 with oxo transfer reactions in catalytic processes.

EXAMPLE IV

SYNTHESIS OF OTHER Mn COMPLEXES ($^nBu_4N)_2$ $[MnPHAB]_2$

To 50 mL of tetrahydrofuran containing 150 mg (0.284 mmol) of $H_4PHAB$ at ambient temperature was added 0.103 g (1 equivalent) of "Bu$_4$N[MnO$_4$] ("Bu$_4$N=n-tetrabutylammonium). The resultant purple solution was stirred for two days. The color changed to a deep maroon within 24 h. The final solution was concentrated by roto-evaporation to a red oil. After vacuum drying for 2 h, a dark, free flowing powder was isolated. The complex was crystallized over 1 week from a 10:1 mixture of DCM and MeCN layered with pentane. [Yield 80% (before crystallization); Elemental analysis for C$_{50}$H$_{60}$O$_4$N$_3$Mn found (calc); C, 73.05 (73.06); H, 7.04 (7.36); N, 5.11 (5.11); FABS-Mass Spectrum mono-anion calculated nominal molecular weight 579 (monomer), found 579; UV/vis extinction in THF @$\lambda_{max}$, nm($\epsilon$, M$^{-1}$cm$^{-1}$); 378 (574), 390 (607), 398 (609), 410 (617), 486 (703); IR of a KBr pellet (amide, cm$^{-1}$); 1624, 1574, 1476, 1448].

"Bu$_4$N[Mn(O)PHAB](2)

To a deep maroon dichloromethane solution of ("Bu$_4$N)$_2$[MnPHAB]$_2$ (100 mg, 0.119 mmol) was added 2 equivalents (0.052 g) of PhIO. The solution turned dark green after approximately 15 min. and stirring was continued for approximately 2 hours at room temperature. The green solution was filtered through Celite (Fisher, Celite 545®), vacuum concentrated, and precipitated with diethyl ether. An air stable, olive green powder was isolated and dried under vacuum for 2 hours. [Yield 69%; Elemental analysis for C$_{50}$H$_{60}$O$_5$N$_3$Mn found 9(calc); C, 70.15(71.66); H, 7.09 (7.22); N, 4.87(5.01); IR of a KBr pellet; 1650 cm$^{-1}$ (vCO) amide, 1471 (vNH)amide, 976 cm$^{-1}$ (vMnO)$_{metal\ oxo}$].

(Et$_4$N)$_2$[KnPHA]$_2$

To 50 mL of dry tetrahydrofuran containing 500 mg (0.946 mmol) of H$_4$PHAB at room temperature was added 0.230 g (1 equivalent) of Et$_4$N[MnO$_4$]. Over a period of 24 hours the solution changed from the familiar purple of permanganate to a maroon color characteristic of the Mn$^{III}$ ligand complex. After two days the solution was vacuum concentrated, filtered in air, and precipitated from the supernatant with diethyl ether and hexane. An impure red powder was collected which was readily crystallized as red, translucent plates (clusters) from a mixture of dichloromethane and pentane at –4° C. [Crude Yield 74%; Elemental analysis for C$_{42}$H$_{44}$N$_3$O$_4$Mn found* (calc*); C, 67.32 (67.64); H, 6.09 (6.49); N, 5.64 (5.63); IR of a KBr pellet (amide cm$^{-1}$) 1626, 1573, 1478, 1446]. *Calculated elemental analysis includes two water molecules per ligand. The found is reported here as an average of two analyses on one crystalline sample.

(Et$_4$N)$_2$[MnMe$_2$PHAB]$_2$

To 50 mL of dry tetrahydrofuran containing 600 mg (1.08 mmol) of H$_4$Me$_2$PHAB was added 0.268 g (1 equivalent) of Et$_4$N[MnO$_4$]. Over a period of 24 hours the solution changed from the permanganate purple to the maroon color characteristic of a Mn$^{III}$ ligand complex. After three days the tetrahydrofuran was removed under reduced pressure, the resulting powder re-dissolved in acetonitrile, and filtered in air. The filtrate was rotoevaporated concentrated and precipitated with diethyl ether and hexane. The complex was readily crystallized as red, translucent parallelepipeds from a mixture of DCM/MeCn (app.3:1) layered with pentane at room temperature. [IR of a KBr pellet (amide cm$^{-1}$) 1620, 1585, 1485, 1444].

EXAMPLE V

SYNTHESIS OF CHROMIUM COMPOUNDS

Ph$_4$P[Cr$^V$(O)PHAB] (3)

A solution of H$_4$PHAB (1.0 g, 1.89 mmol) in 75 mL THF was frozen in liquid nitrogen. 4.7 mL tert-butyl lithium (1.7M in pentane, 8.0 mmol) was added via syringe and the solid mass was allowed to thaw. Upon complete melting, anhydrous CrCl$_2$ (0.39 g, 3.19 mmol) was added directly and the nitrogen atmosphere restored immediately. The solution was stirred at room temperature for 1 hr; during this period all the CrCl$_2$ dissolved. The solution was cooled to 0° C. and 5.5 mL of tert-butylhydroperoxide (3M in pentane, 16.4 mmol) was added over a two minute period via a teflon syringe, upon which the solution turns a deep red-brown color. The solution was warmed to room temperature, stirred for 30 minutes, filtered through a pad of Celite and concentrated to approximately 25 mL. Addition of 50 mL diethyl ether and 50 mL pentane precipitated the crude product, Li[Cr$^V$(O)PHAB]. The light brown supernatant was decanted off with a cannula, the precipitate washed with 10 mL pentane and dried in vacuo for 15 minutes to yield 0.83 g (81% yield) of the Li salt. Metathesis with Ph$_4$PCl (1.0 g, 2.6 mmol) in 35 mL CH$_2$Cl$_2$ and 15 mL MeCN, filtration through a pad of Celite and concentration in vacuo result with a crude product which was recrystallized from 60 mL Ch$_2$Cl$_2$ carefully layered with 60 mL diethyl ether. After 2–3 days, dark red brown crystals of Ph$_4$P[Cr$^V$(O)PhBABO] were collected. Yield 0.33 g (25.4%). Analysis calculated for C$_{58}$H$_{44}$N$_2$O$_5$P$_1$Cr$_1$: C, 74.74; H, 4.76; N 3.00. Found: C, 74.75; H, 4.74.; N, 305. IR (KBr pellet); "amide CO=1642 cm$^{-1}$, "Cr(O)=986 cm$^{-1}$. FAB-MS (anion): calculated nominal molecular weight for [Cr(O)(PHAB]-592 amu, found 592 amu. UV-vis (CH$_2$Cl$_2$): $\lambda_{max}$(nm)($\epsilon$, cm$^{-1}$M$^{-1}$) 360 (4140), 516sh (605), 624sh (342).

Pr$_4$N[Cr$^V$(O) (DAMA)$_2$]

Tridentate ligand (DAMA) was dissolved in tetrahydrofuran (30 mL), frozen, and 3 equivalents of tert-butyllithium (Aldrich, 1.7M in pentane) were added. The solid was allowed to melt, at which point anhydrous CrCl$_2$ (Aldrich, 116 mg) was added and the solution was allowed to warm to room temperature. After an hour of stirring at room temperature, tert-butylhydroperoxide (Aldrich, 3M in pentane, 2 eq) was added, resulting in a dark green solution. After 1 hour, solvent was removed under reduced pressure and the solid redissolved in a dichloromethane/ethanol mixture. To this solution was added Pr$_4$NBr (Aldrich, 2 equivalents, 1.3 g) and the solution stirred for several hours. The solvent was again removed under reduced pressure and the solid redissolved in absolute ethanol. Slow evaporation of the ethanol at room temperature yields crystals. [Elemental analysis for C$_{62}$H$_{78}$N$_5$O$_8$Cr found (calc); C, 69.54 (69.38); H, 7.37 (7.32); N, 6.57 (6.52)]

EXAMPLE VI

SYNTHESIS OF RUTHENIUM COMPOUNDS

"Pr$_4$N [Ru(O)PHAB]

To 200 mg (0.378 mmol) of H$_4$PHAB in 30 mL of tetrahydrofuran was added 0.133 g (1 equivalent) of TPAP (Aldrich, tetrapropylammonium perruthenate). The solution immediately turned dark. After stirring overnight, the solution was filtered in air. The precipitate collected was fairly pure "Pr$_4$N[Ru(O)PHAB]. The filtrate was rotoevaporated concentrated and the product mixture precipitated by addition of hexane and diethyl ether. The solids (treated separately) were redissolved in acetonitrile and allowed to slowly evaporate, yielding crystalline "Pr$_4$N[Ru(O)(PHAB]. [Yield 30%; Elemental analysis for C$_{46}$H$_{52}$N$_3$O$_5$Ru found (calc.½ H$_2$O); C, 66.02 (66.01); H, 6.23 (6.32); N, 5.14 (5.02); IR of a KBr pellet (v$_{C=O}$cm$^{-1}$) 1634, 1670; (V$_{M=O}$) 887; FABS-Mass Spectrum anion calculated nominal molecular weight/charge 642, found 642; crystal structure].

[Ru(O)PHAB]

To 100 mg of "Pr$_4$N[Ru(O)PHAB] in 30 mL of dry dichloromethane were added 0.0662 g (1 equivalent) of ceric ammonium nitrate. The solution was stirred for 3 hours, resulting in a dark solution. This solution was filtered in air to remove any cerium precipitate and the filtrate rotoevaporated concentrated to an oil. The oil was redissolved in a minimum of acetone (reagent grade, Fisher) and placed at −4° C. overnight to yield crystals. [Yield 65%; Elemental analysis for $C_{37}H_{30}N_2O_6Ru$ found (calc.½ $H_2O$); C. 62.39 (62.70); H. 3.93 (4.41); N. 4.34 (3.95); IR of a KBr pellet ($v_{C=O}cm^{-1}$) 1704; ($V_{M=O}$) 928; FAB-MS cation calculated nominal molecular weight/charge 643, found 643; crystal structure].

$Pr_4N[Ru(O)BP\text{-}PHAB]$

To a tetrahydrofuran solution of 400 mg of $H_4BP\text{-}PHAB$ was added 1 equivalent (232 mg) of tetrapropyl ammoniumperruthenate. The mixture was stirred overnight, giving a dark solution. The solution was rotoevaporated concentrated to an oil and redissolved in a minimum of acetone. The acetone solution was placed at −80% C from which crude crystalline material could be isolated after several days. The crystals were recrystallized from a diethyl ether/acetone solution at −4° C. to obtain pure material. [Elemental analysis for $C_{52}H_{56}N_3O_5Ru$ found (calc); C. 68.32 (69.09); H. 6.10 (6.24); N. 4.54 (4.65), IR of a KBr pellet, carbonyl @1668, 1629 $cm^{-1}$, metal oxo @886 $cm^{-1}$; Anionic FABS-Mass Spectrum calculated nominal molecular weight/charge 718, found 718].

EXAMPLE VII

SYNTHESIS OF IRON COMPOUNDS $(Et_4N)$ (Li) $[Fe(Cl)PHAB].H_2O$

To a frozen tetrahydrofuran solution of $H_4PHAB$ (500 mg, 0.946 mmol) was added 4.2 equivalents (2.34 mL) of tert-butyllithium (Aldrich, 1.7M in pentanes). The solution was then allowed to warm to its melting point, at which point 1 equivalent of $Et_4N[FeCl_4]$ was added. The mixture was stirred for several hours at ambient temperature, giving a large amount of a light green precipitate and a red solution. The solution was vacuum concentrated, precipitated with hexanes, re-dissolved in a minimum of acetonitrile and filtered in air. Red, x-ray quality crystals were obtained by vapor diffusion of diethyl ether into the resultant acetonitrile solution of the original precipitate. The crystals were collected by decanting off the mother liquor, washing 3 times with diethyl ether to remove any non-crystalline particles, filtration, and then drying for 2 hours under vacuum. [Yield 67%; Elemental analysis for $LiC_{42}H_{46}O_5N_3ClFe$ found (calc*); C. 63.92(63.92); H. 5.91(6.13); N. 5.30(5.32); Cl. 4.74(4.44); FABS anion calculated nominal molecular weight/charge 622, found 622; IR of a KBr Pellet (amide $cm^{-1}$); 1604, 1566, 1470, 1445; corrected µeff(295 K)=5.91 BM (spin only µeff=5.92 BM); crystal structure]. Calculated includes two water molecules per Fe, the complex is hygroscopic.

$(Et_4N)$ (Li) $[Fe(Cl)Me_2PHAB]$

To 400 mg (0.719 mmol) of $H_4Me_2PHAB$ in 20 mL of dry, frozen tetrahydrofuran was syringed 1.69 mL (4 equivalents) of tert-butyllithium. The reaction tube was removed from the liquid nitrogen and allowed to slowly warm up. Just as all the tetrahydrofuran melted 0.236 g (1 equivalent) of $Et_4NFeCl_4$ was added and the solution stirred under nitrogen overnight. The next day the tetrahydrofuran was removed under vacuum and the resulting solid was re-dissolved in acetonitrile and filtered in air. Diethyl ether was allowed to vapor diffuse with the filtrate, giving dark crystals. [Crude yield 43%; IR of a KBr pellet (amide $cm^{-1}$) 1609, 1577, 1482, 1446].

EXAMPLE VIII

SYNTHESIS OF RHENIUM

Synthesis of $Ph_4P[Re(O)PHAB]$ 500 mg of $H_4PHAB$ were placed in dry tetrahydrofuran and frozen under nitrogen. To the frozen solution was added 1 equivalent of tert-butyllithium (2.5 mL, Aldrich) via syringe. The solution was allowed to warm to the solvent (tetrahydrofuran) melting point (−−108° C.) at which point $Ph_4PRe(O)Cl_4$ (1 equivalent, 550 mg)$^{ref}$ was added. After stirring overnight a light tan precipitate was collected by filtration (510 mg, 52% yield) and dried under vacuum. The product was crystallized by vapor diffusion of diethyl ether into a chloroform solution yielding brown plates. [Elemental Analysis for $C_{58}H_{44}O_5N_2PRe$ found (calculated); C. 63.15 (65.34); H. 4.10 (4.15); N. 2.35 (2.62): FABS-mass spectrum of anion, calculated molecular weight/charge 727, found 727].

This method is readily amenable to replacement of the rhenium starting material with an analogous technetium complex to form the technetium oxo analog described above. Another method would be analogous to our method of ruthenium insertion into the ligand using a high valent oxo complex (i.e., substituting pertechnetate for perruthenate).

Rhenium and technetium metal oxo complexes are used as radio imaging agents. Tc-99m. is a high energy gamma-emitter that has been used for radio imaging for more than a decade. (Bossuyt et al., 1991). Rhenium-186 and rhenium-188 are less energetic beta emitters which may be beneficial replacements for the higher energy gamma emitters in some circumstances (Callahan et al., 1988). Many current radiopharmaceuticals employ $N_2S_2$ chelating systems similar to the $N_2O_2$ scheme of PHAB (Walovitch et al., 1991).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anderson & Kochi, J. Am. Chem. Soc., 92:2450, 1970.
Anson et al., J. Am. Chem. Soc., 109:2974, 1987.
Bossek et al., J. Am. Chem. Soc., 112:6387, 1990.
Bossuyt et al., J. Nucl. Med., 32:299, 1991.
Callahan & Bremer, J. Nucl. Med., 29:847, 1988.
Chandra & Chakravorty, Inorg. Chem., 31:760, 1992.
Collins & Gordon-Wylie, J. Am. Chem. Soc., 111:4511, 1989.
Collins et al., J. Am. Chem. Soc., 112:899, 1990.
Collman et al., J. Am. Chem. Soc., 97:1427, 1975.
Ellis & Lyons, Catal. Lett., 8:45, 1991.

Garcia-Deibe et al., *J. Chem. Soc., Chem. Commun.*, 728, 1991.
Ghodes & Armstrong, *Inorg. Chem.*, 31:368, 1992.
Holm, *Chem. Rev.* 87:1401–1449, 1987.
Ingraham & Meyer, *Biochemistry of Dioxygen*, Plenum Press: New York, 1985.
Jacobsen et al., *J. Am. Chem. Soc.* 113:6703–6704, 1991.
Jones et al., *Chem. Rev.*, 79:139, 1979.
Larson et al., *Inorg. Chem.*, 31:373, 1992.
Larson & Pecoraro, *J. Am. Chem. Soc.*, 113:3810, 1991.
Lee et al., *Tetrahedron Letters*, 32:5055, 1991.
MacDonnell et al., *J. Am. Chem. Soc.*, 116(16):7431–7432, 1994.
Mazzi et al., *Technetium and Rhenium in Chemistry and Nuclear Medicine*, 39–50, 1990.
Mukaiyama et al., *Chem. Lett.*, 327–330, 1993.
Nishida et al., *Naturforsh.*, 43b:472, 1988.
Sheldon & Kochi, *Metal Catalyzed Oxidations of Organic Compounds*, Academic Press: New York, 1981.
Siddall et al., *J. Chem. Soc., Chem. Commun.*, 1185, 1983.
Spiro, T. G., Ed., *Metal Ion Activation of Dioxygen*, John Wiley & Sons: New York, 1980.
Srinivasan & Kochi, *Inorg. Chem.*, 24:4671–4679, 1985.
Steinfeld et al., *Chemical Kinetics and Dynamics*, Prentice Hall: New Jersey, 182–184, 1989.
Vincent et al., *Inorg. Chem.*, 25:996, 1986.
Walovitch et al., *Neuropharmacology*, 30:283, 1991.
Workman et al., *Inorg. Chem.*, 31:1550, 1992.
Yu et al., *Inorg. Chem.*, 30:4067, 1991.
Collins et al., U.S. Pat. No. 4,577,042, Mar. 18, 1986. Homogeneous Coordination Compounds as Oxidation Catalysts.

What is claimed is:

1. A compound that complexes a metal to form a coordination complex, said compound having the structure:

wherein the substiutents $R_1$–$R_4$ are independently phenyl, t-butyl, neopentyl, trimethyl, silyl or cyclohexyl and wherein Y is a phenyl, substituted phenyl, biphenyl, substituted biphenyl including chiral binapthol, napthol, and substituted naphthol, and wherein Y has bonds to said two nitrogens in said structure with said nitrogens positioned at ortho positions relative to carbons of Y to provide a structure that is effective to form a tetradentate complex with said metal, and X is separately or in combination a hydroxyl, amino, thiol.

2. The compound of claim 1, wherein Y is phenyl.

3. The compound of claim 2, wherein $R_1$–$R_4$ are phenyl.

4. The compound of claim 3, further defined as bis 1,2-(2,2-diphenyl-2-hydroxyethanamido) benzene.

5. The compound of claim 1, wherein Y is biphenyl.

6. The compound of claim 5, wherein $R_1$–$R_4$ are phenyl.

7. The compound of claim 6, further defined as 2,2'-bis (2-hydroxy-2,2-diphenylethanamido) biphenyl.

8. A compound that complexes a metal to form a coordination complex, said compound having the structure:

wherein the substiutents $R_1$–$R_4$ are independently phenyl, t-butyl, neopentyl, trimethyl silyl or cyclohexyl and wherein Y is alkyl or substituted ayyl and wherein Y has bonds to said two nitrogens in said structure to provide a structure that is effective to form a tetradentate complex with said metal, and X is independently a hydroxyl, amino, or thiol.

* * * * *

UNITED STATES PATENT AND TRADEMARK OFFICE
CERTIFICATE OF CORRECTION

PATENT NO. : 5,786,496
DATED : July 28, 1998
INVENTOR(S) : Thomas V. O'Halloran, et al It is certified that error appears in the above-indentified patent and that said Letters Patent is hereby corrected as shown below:

Col. 18, line 2; after "trimethyl" delete the comma.

line 36; replace "ayyl" with ---alkyl---.

Signed and Sealed this

Second Day of March, 1999

Attest:

Q. TODD DICKINSON

*Attesting Officer*       *Acting Commissioner of Patents and Trademarks*